US008951276B2

(12) United States Patent
Kellerman et al.

(10) Patent No.: US 8,951,276 B2
(45) Date of Patent: Feb. 10, 2015

(54) SYSTEMS AND METHODS FOR PERCUTANEOUS INTRAVASCULAR ACCESS AND GUIDEWIRE PLACEMENT

(71) Applicant: Caymus Medical, Inc., San Juan Capistrano, CA (US)

(72) Inventors: Brad M. Kellerman, Escondido (CA); Jeffrey E. Hull, Midlothian, VA (US); David K. Wrolstad, Yucaipa, CA (US)

(73) Assignee: Avenu Medical, Inc., San Juan Capistrano, CA (US)

( * ) Notice: Subject to any disclaimer, the term of this patent is extended or adjusted under 35 U.S.C. 154(b) by 49 days.

(21) Appl. No.: 13/668,190

(22) Filed: Nov. 2, 2012

(65) Prior Publication Data

US 2013/0123827 A1    May 16, 2013

Related U.S. Application Data

(60) Provisional application No. 61/556,128, filed on Nov. 4, 2011.

(51) Int. Cl.
*A61B 17/34*        (2006.01)
*A61B 17/11*        (2006.01)

(52) U.S. Cl.
CPC ......... *A61B 17/3403* (2013.01); *A61B 17/3468* (2013.01); *A61B 17/3478* (2013.01); *A61B 2017/1139* (2013.01); *A61B 2017/3454* (2013.01)
USPC ........................................................ 606/185

(58) Field of Classification Search
USPC ............. 604/164.01, 164.06, 164.09, 164.11, 604/164.13; 606/167, 170, 185
See application file for complete search history.

(56) References Cited

U.S. PATENT DOCUMENTS

| 5,290,278 | A  | 3/1994  | Anderson      |
| 5,425,731 | A  | 6/1995  | Daniel et al. |
| 5,830,222 | A  | 11/1998 | Makower       |
| 5,830,224 | A  | 11/1998 | Cohn et al.   |
| 5,910,133 | A  | 6/1999  | Gould         |
| 6,068,637 | A  | 5/2000  | Popov et al.  |
| 6,068,638 | A  | 5/2000  | Makower       |
| 6,071,292 | A  | 6/2000  | Makower et al.|
| 6,083,223 | A  | 7/2000  | Baker         |
| 6,099,542 | A  | 8/2000  | Cohn et al.   |
| 6,190,353 | B1 | 2/2001  | Makower et al.|

(Continued)

OTHER PUBLICATIONS

International Search Report and Written Opinion, corresponding to PCT/US2012/063444, International filing date Nov. 2, 2012.

*Primary Examiner* — Jonathan W Miles
(74) *Attorney, Agent, or Firm* — Donald E. Stout; Stout, Uxa & Buyan, LLP

(57) ABSTRACT

A device for allowing passage of a guidewire from a primary blood vessel to an adjacent secondary blood vessel includes a main body having a primary lumen and a secondary lumen, and a piercing member disposed in the secondary lumen, and configured to be moved distally out of the secondary lumen, and to pierce through tissue while being distally moved. A third lumen located within the piercing member is configured to allow placement of a guidewire from the primary blood vessel to the adjacent secondary blood vessel. In one embodiment, the secondary lumen is configured to allow articulation of the distal end of the piercing element. The piercing member has a sharp point on one end to facilitate cutting a small communicating aperture from the primary blood vessel to the secondary blood vessel.

8 Claims, 12 Drawing Sheets

(56) References Cited

U.S. PATENT DOCUMENTS

| | | |
|---|---|---|
| 6,235,027 B1 | 5/2001 | Herzon |
| 6,248,117 B1 | 6/2001 | Blatter |
| 6,283,983 B1 | 9/2001 | Makower et al. |
| 6,302,875 B1 | 10/2001 | Makower et al. |
| 6,330,884 B1 | 12/2001 | Kim |
| 6,375,615 B1 | 4/2002 | Flaherty et al. |
| 6,379,319 B1 | 4/2002 | Garibotto et al. |
| 6,398,797 B2 | 6/2002 | Bombard et al. |
| 6,464,665 B1 | 10/2002 | Heuser |
| 6,533,778 B2 | 3/2003 | Herzon |
| 6,561,998 B1 | 5/2003 | Roth et al. |
| 6,579,311 B1 | 6/2003 | Makower |
| 6,613,081 B2 | 9/2003 | Kim et al. |
| 6,616,675 B1 | 9/2003 | Evard et al. |
| 6,669,709 B1 | 12/2003 | Cohn et al. |
| 6,699,245 B2 | 3/2004 | Dinger et al. |
| 6,709,444 B1 | 3/2004 | Makower |
| 6,726,677 B1 | 4/2004 | Flaherty et al. |
| 6,863,684 B2 | 3/2005 | Kim et al. |
| 6,908,463 B2 | 6/2005 | Treat et al. |
| 6,929,009 B2 | 8/2005 | Makower et al. |
| 7,056,325 B1 | 6/2006 | Makower et al. |
| 7,159,592 B1 | 1/2007 | Makower et al. |
| 7,191,015 B2 | 3/2007 | Lamson et al. |
| 7,316,655 B2 | 1/2008 | Garibotto et al. |
| 7,351,247 B2 | 4/2008 | Kupiecki et al. |
| 7,387,636 B2 | 6/2008 | Cohn et al. |
| 7,588,566 B2 | 9/2009 | Treat et al. |
| 7,729,738 B2 | 6/2010 | Flaherty et al. |
| 7,846,172 B2 | 12/2010 | Makower |
| 2003/0100920 A1 | 5/2003 | Akin et al. |
| 2006/0111704 A1 | 5/2006 | Brenneman et al. |
| 2006/0142788 A1 | 6/2006 | Wilson et al. |
| 2008/0065019 A1 | 3/2008 | Heuser et al. |

# SYSTEMS AND METHODS FOR PERCUTANEOUS INTRAVASCULAR ACCESS AND GUIDEWIRE PLACEMENT

This application claims the benefit under 35 U.S.C. 119(e) of the filing date of Provisional U.S. Application Ser. No. 61/556,128, entitled Systems and Methods for Percutaneous Intravascular Access and Guidewire Placement, filed on Nov. 4, 2011. This application is also related to commonly owned U.S. patent application Ser. No. 13/161,183, entitled Systems and Methods for Creating Arteriovenous (A Fistulas, and U.S. patent application Ser. No. 13/161,356, entitled Intravascular Arterial to Venous Anastomosis and Tissue Welding Catheter, both filed on Jun. 15, 2011. All of the foregoing applications are expressly incorporated herein by reference, in their entirety.

BACKGROUND OF THE INVENTION

In the body, various fluids are transported through conduits throughout the organism to perform various essential functions. Blood vessels, arteries, veins, and capillaries carry blood throughout the body, carrying nutrients and waste products to different organs and tissues for processing. Bile ducts carry bile from the liver to the duodenum. Ureters carry urine from the kidneys to the bladder. The intestines carry nutrients and waste products from the mouth to the anus.

In medical practice, there is often a need to connect conduits to one another or to a replacement conduit to treat disease or dysfunction of the existing conduits. The connection created between conduits is called an anastomosis.

In blood vessels, anastomoses are made between veins and arteries, arteries and arteries, or veins and veins. The purpose of these connections is to create either a high flow connection, or fistula, between an artery and a vein, or to carry blood around an obstruction in a replacement conduit, or bypass. The conduit for a bypass is a vein, artery, or prosthetic graft.

An anastomosis is created during surgery by bringing two vessels or a conduit into direct contact. The vessels are joined together with suture or clips. The anastomosis can be end-to-end, end-to-side, or side-to-side. In blood vessels, the anastomosis is elliptical in shape and is most commonly sewn by hand with a continuous suture. Other methods for anastomosis creation have been used including carbon dioxide laser, and a number of methods using various connecting prosthesis, clips, and stents.

An arterio-venous fistula (AVF) is created by connecting an artery to a vein. This type of connection is used for hemodialysis, to increase exercise tolerance, to keep an artery or vein open, or to provide reliable access for chemotherapy.

An alternative is to connect a prosthetic graft from an artery to a vein for the same purpose of creating a high flow connection between artery and vein. This is called an arterio-venous graft, and requires two anastomoses. One is between artery and graft, and the second is between graft and vein.

A bypass is similar to an arteriovenous graft. To bypass an obstruction, two anastomoses and a conduit are required. A proximal anastomosis is created from a blood vessel to a conduit. The conduit extends around the obstruction, and a second distal anastomosis is created between the conduit and vessel beyond the obstruction.

As noted above, in current medical practice, it is desirable to connect arteries to veins to create a fistula for the purpose of hemodialysis. The process of hemodialysis requires the removal of blood from the body at a rapid rate, passing the blood through a dialysis machine, and returning the blood to the body. The access to the blood circulation is achieved with (1) catheters placed in large veins, (2) prosthetic grafts attached to an artery and a vein, or (3) a fistula where an artery is attached directly to the vein.

Hemodialysis is required by patients with kidney failure. A fistula using native blood vessels is one way to create high blood flow. The fistula provides a high flow of blood that can be withdrawn from the body into a dialysis machine to remove waste products and then returned to the body. The blood is withdrawn through a large access needle near the artery and returned to the fistula through a second large return needle. These fistulas are typically created in the forearm, upper arm, less frequently in the thigh, and in rare cases, elsewhere in the body. It is important that the fistula be able to achieve a flow rate of 500 ml per minute or greater, in order for the vein to mature or grow. The vein is considered mature once it reaches >4 mm and can be accessed with a large needle. The segment of vein in which the fistula is created needs to be long enough (>6 cm) to allow adequate separation of the access and return needle to prevent recirculation of dialysed and non-dialysed blood between the needles inserted in the fistula.

Fistulas are created in anesthetized patients by carefully dissecting an artery and vein from their surrounding tissue, and sewing the vessels together with fine suture or clips. The connection thus created is an anastomosis. It is highly desirable to be able to make the anastomosis quickly, reliably, with less dissection, and with less pain. It is important that the anastomosis is the correct size, is smooth, and that the artery and vein are not twisted.

SUMMARY OF THE INVENTION

The present disclosed invention eliminates the above described open procedures, reduces operating time, and allows for a consistent and repeatable fistula creation.

The present invention comprises a device to allow passage of a guidewire from a primary blood vessel to an adjacent secondary blood vessel, which comprises a main body having a primary lumen and a secondary lumen and a piercing member disposed in the secondary lumen, and configured to be moved distally out of the secondary lumen, and to pierce through tissue while being distally moved. A third lumen located within the piercing member is configured to allow placement of a guidewire from the primary blood vessel to the adjacent secondary blood vessel.

In one embodiment, the secondary lumen is constructed out of superelastic material, such as Nitinol, that is shaped such that the distal tip is oriented toward the adjacent secondary blood vessel. The secondary lumen may have a "J" shape heat set into the secondary lumen; however, different shapes may be used depending upon the type of anatomy that is being accessed. The primary lumen is configured with a stiffness such that it has the ability to straighten the shape of the secondary lumen. Either advancing or retracting the primary lumen relative to the secondary lumen can adjust the rise, or shape, of the secondary lumen. Shaping the primary lumen can further modify the angle at which the piercing member exits the secondary lumen. In an alternative embodiment, the shape of the secondary lumen may be modified using a tendon wire. In still another embodiment, the piercing member is designed to remain in a substantially straight configuration.

In another aspect of the invention, the distal tip of the secondary lumen has a feature to make it such that it will not perforate the primary lumen as it is being placed into a desired position within the body. In the first embodiment noted above, the tip has a large diameter polymer tip that has a rounded distal edge and is atraumatic. This distal tip also has features that make it visible under different imaging techniques, such as ultrasound, fluoroscopy, CT, or MRI. There is a coil constructed of a radiopaque material, embedded in the polymer tip. Small particles of air or other radiopaque materials known to those skilled in the art can also be used to increase the radiopacity of the tip.

The hollow piercing member has a sharp point on the distal tip that exits from the primary vessel by puncturing its wall and enters into the secondary vessel in the same manner. In one embodiment, the sharp distal point is constructed using a lancet point. The primary bevel is ground at an angle between 12 and 20 degrees with a secondary angle between 5-20 degrees, with a rotation angle between 25-45 degrees. The needle grind is designed such that it pierces through the vessel wall and does not core, or cut a plug, through the vessel wall, to minimize bleeding between vessels when removed after the guidewire is placed into the secondary vessel. The outer diameter of the piercing member is also minimized to further reduce bleeding. The piercing member is oriented within the secondary lumen such that the tip of the lancet point is directed toward the adjacent secondary vessel. Other piercing mechanisms, or needle point grind configurations, known to those skilled in the art may be provided.

More particularly, there is provided a device for creating intravascular access and guidewire placement, which comprises a main body having a first lumen, a piercing member disposed in that lumen, and configured to be moved distally out of said lumen and to pierce through tissue while being distally moved, and a handle attached to the main body and having an actuator for moving the piercing member. A second lumen is disposed within the piercing member. A guidewire is disposed in the second lumen for delivery into a desired site from a distal end of the second lumen. The piercing member has a sharp point on one end thereof.

In one disclosed embodiment, a third lumen is disposed within the main body, outwardly of the first lumen. The piercing member is retractable into the first lumen. The third lumen is defined by a needle guide having shape memory properties, the needle guide being actuatable to a curved orientation by adjustment of a position of the main body to create an incrementally adjustable radius of curvature on the needle guide. The piercing member has shape memory properties, and is actuatable to create an incrementally adjustable radius of curvature.

The actuator for moving the piercing needle linearly comprises a slide. In the curved embodiment, a second actuator is disposed on the handle for actuating the needle guide to a curved orientation. This actuator comprises a rotatable knob. In both embodiments, the first lumen is defined by a needle guide having an atraumatic distal tip having a relatively large diameter. The atraumatic distal tip is comprised of a polymer material and further comprises radiopaque materials. Preferably, the radiopaque materials comprise a plurality of coils constructed of a radiopaque material.

The sharp point preferably comprises a lancet point and primary bevels.

In another aspect of the invention, there is disclosed a method of creating intravascular access and guidewire delivery, which comprises steps of positioning the main body of a device within a primary vessel and manipulating a distal end of the device to engage an inner wall of the primary vessel and to push the primary vessel into close engagement with an adjacent secondary vessel. Yet another step comprises extending the piercing member distally from the main body, through the wall of the primary vessel, and through an adjacent wall of the secondary vessel, so that the end of the piercing member is disposed within the secondary vessel for creating a communicating aperture on the opposing walls of the primary and secondary vessel.

In one embodiment, the method comprises a further step of incrementally adjusting a radius of curvature of the piercing member. In both embodiments, the positioning step is performed percutaneously.

The method further comprises a step of advancing a guidewire distally through a lumen in the piercing member from the primary vessel into the secondary vessel, and a step of withdrawing the device from the vessel, thus leaving the guidewire in place and crossing from the primary vessel to the secondary vessel through said communicating aperture.

In still another aspect of the invention, a method of creating a passage between adjacent primary and secondary blood vessels is disclosed, comprising a step of positioning a main body of the device within the primary vessel and extending a piercing member distally from the main body, through the wall of the primary vessel, and through an adjacent wall of the secondary vessel, so that the piercing member is disposed within the secondary vessel. The secondary lumen is linearly actuated to move relative to a distal end of the piercing member for articulating the distal end of the piercing member for cutting a small communicating aperture from the primary blood vessel to the adjacent secondary blood vessel. The method further comprises the step of advancing a guidewire distally within the piercing element to pass from the primary blood vessel, while maintaining position substantially within the primary blood vessel, to the adjacent secondary blood vessel.

The invention, together with additional features and advantages thereof, may best be understood by reference to the following description taken in conjunction with the accompanying illustrative drawings.

DESCRIPTION OF THE PREFERRED EMBODIMENT

Figure 1A:
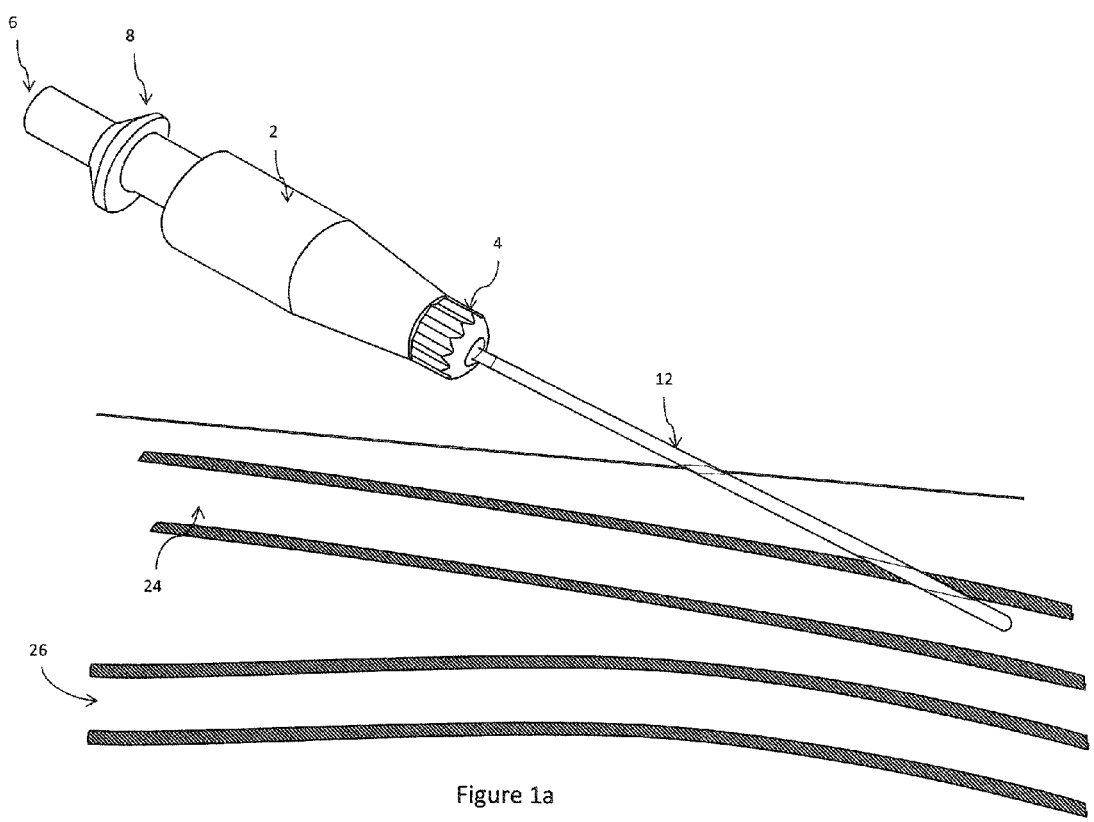
FIG. 1a is a view of one embodiment of the device of the present invention, wherein the device has been percutaneously or surgically positioned at a desired location in a blood vessel.
Figure 1B:
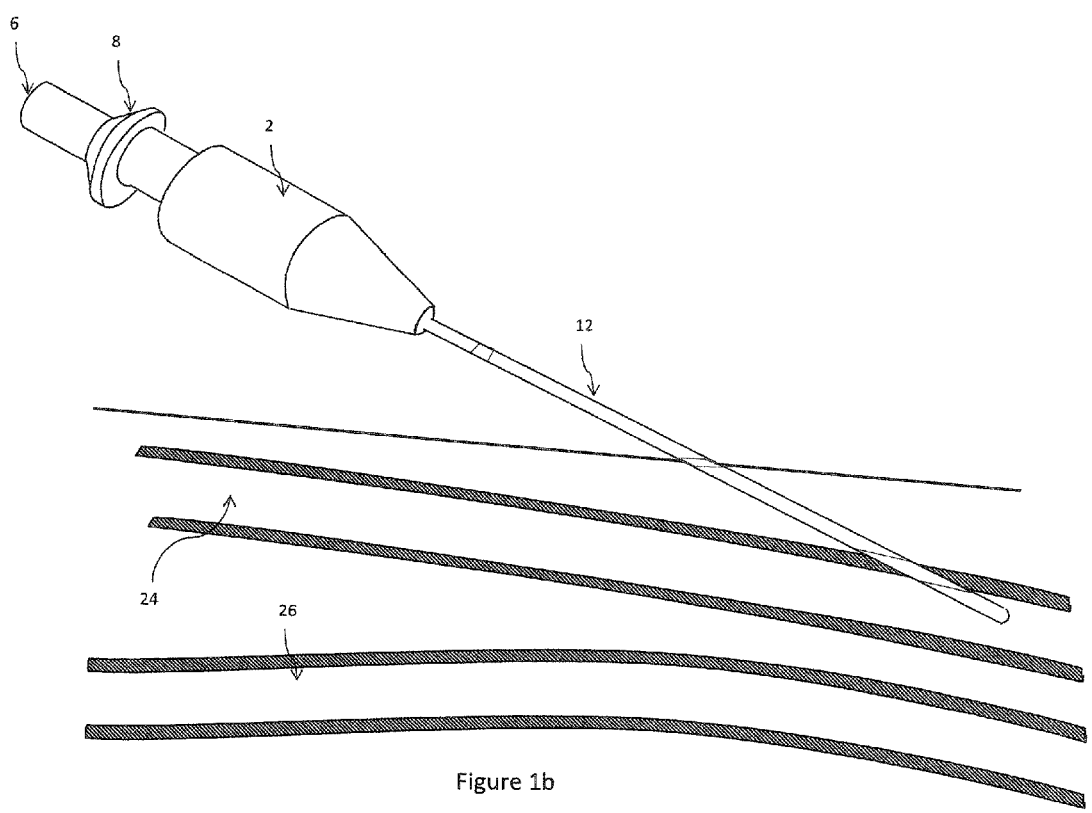
FIG. 1b is a view, similar to FIG. 1a, of another embodiment of the device of the present invention, wherein the device has been percutaneously or surgically positioned at a desired location in a blood vessel.

Referring now more particularly to the drawings shown in FIGS. 1a-7, there are illustrated several embodiments of a device and system constructed in accordance with the principles of the present invention. As illustrated in FIG. 1a, one embodiment of the device 10 comprises a handle or handpiece 2 and a main body shaft 12 having a primary lumen 18 and a secondary lumen 14 (FIG. 2a). To begin the inventive method of intravascular access and communication, the practitioner selects an appropriate procedural site having each of a primary blood vessel 24 and a secondary blood vessel 26 (FIG. 1) in close proximity to one another. In currently preferred approaches, the primary blood vessel 24 comprises a vein, and the secondary blood vessel 26 comprises an artery, but the invention is not limited to this arrangement. The main body 12 is inserted into primary vessel 24 so that the distal end 32 thereof (FIG. 2a) lies within the blood flow passage of the primary vessel. Preferably, this insertion step is performed using percutaneous technique, but open surgery may also be employed.

Figure 2A:
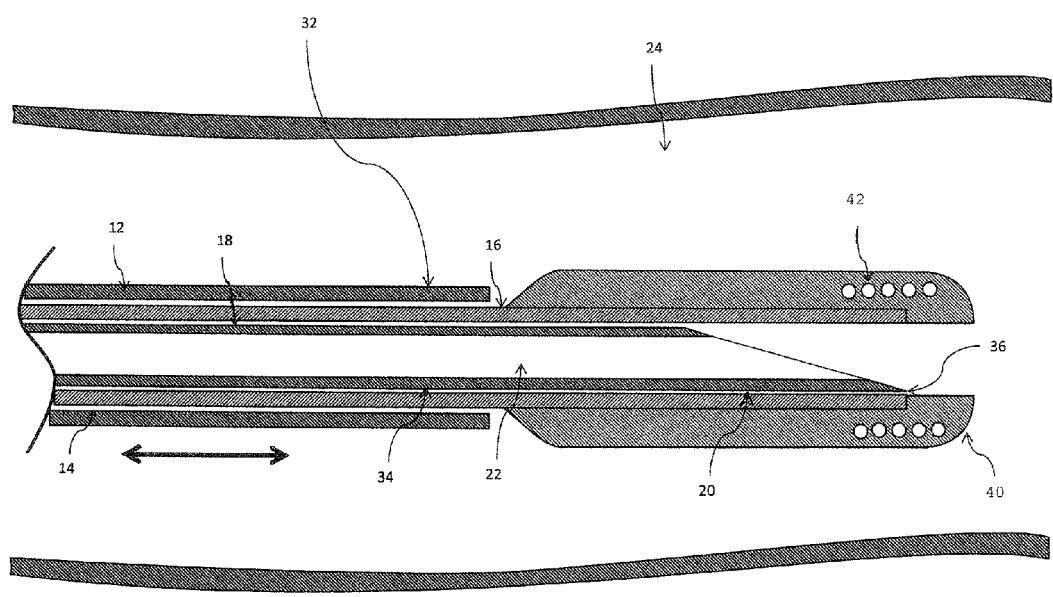
FIG. 2a is a view of the FIG. 1a embodiment of the present invention, illustrating the distal piercing element in isolation.
Figure 2B:
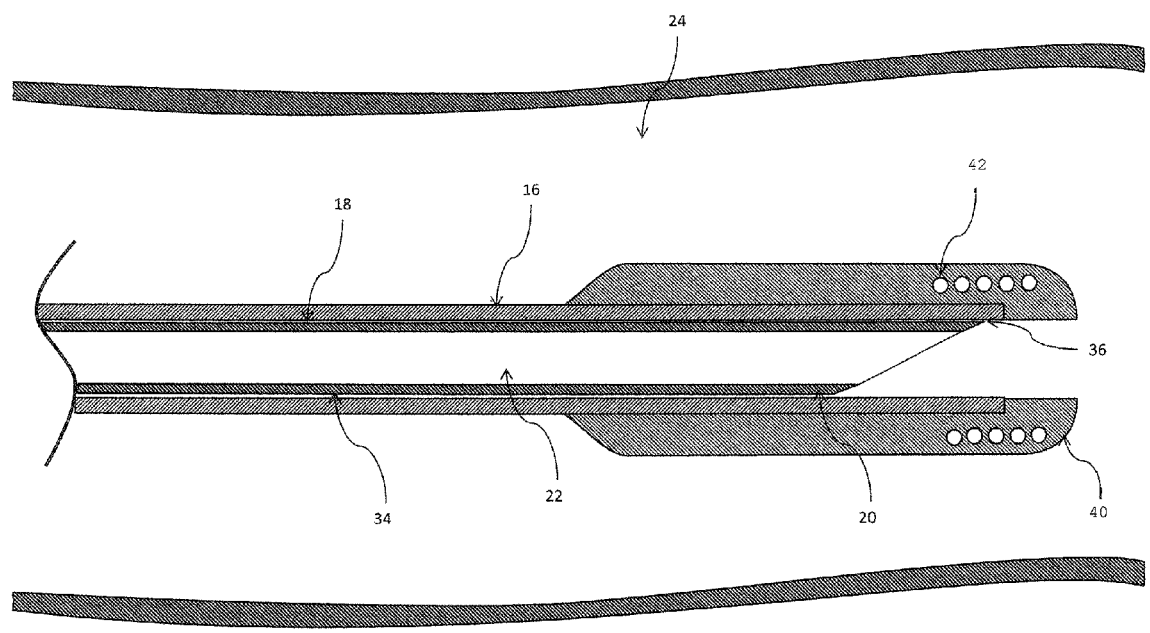
FIG. 2b is a view, similar to FIG. 2a, of the embodiment of FIG. 1b, illustrating the distal piercing element in isolation.

With reference now to FIG. 2a, a piercing element 20 comprises a needle guide 34, lumen 22, and a distal tip 36, and can be adjustably oriented axially within the secondary lumen 14 of a needle guide 16. These elements are further adjustably oriented axially within lumen 18 of the needle guide 16, and lumen 22 provides an externally communicating passage. A distal end 40 of the needle guide 16 comprises a blunt large diameter atraumatic tip, comprised of a polymer material, having a rounded distal edge. This distal tip 40 also has features that make it visible under different imaging techniques, such as ultrasound, fluoroscopy, CT, or MRI. There is a coil 42 constructed of a radiopaque material, embedded in the polymer tip 40. Small particles of air or other radiopaque materials known to those skilled in the art may also be used to increase the radiopacity of the tip.

Figure 3A:
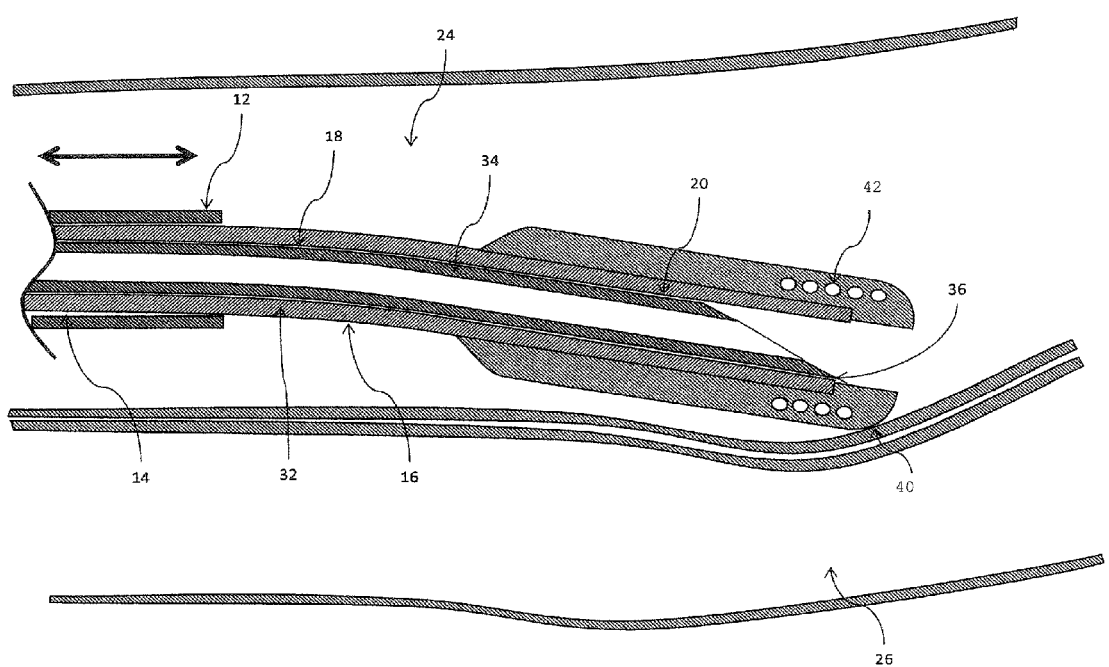
FIG. 3a is a view similar to FIG. 2a, wherein the distal piercing element of FIG. 2a has been advanced distally to push the blood vessel in which it is disposed into contact with the adjacent blood vessel.

Referring to FIGS. 2a and 3a, the blunt tip 40 is manipulated to contact an inner wall of the primary vessel and to push it into desired engagement with the adjacent wall of the secondary vessel, as shown in FIG. 3a. The position of desired engagement is arranged to optimize the piercing step to be next described. The distal tip 36 of the piercing element 20 may be longitudinally extended with respect to the needle guide 34, between a range of the radius of curvature along axis 35 of needle guide 34, using a slide 8 on the handle 2. A first, or retracted, position is illustrated in FIG. 2a, where the distal tip 36 is within the secondary lumen 14 of needle guide 16. As will be described more fully below, the retracted orientation is utilized during the initial device insertion steps, as well as the device withdrawal steps, while variable extended orientations are the operative orientation for creating the communication passageway and guidewire placement. Needle guide 34 of piercing element 20 is fabricated of a material that has shape memory properties that allow it to be held in an essentially axial position indefinitely by needle guide 16, while in the orientation shown in FIG. 2a, and can achieve an incremental increase in the radius of curvature as distal tip 36 is extended beyond the end of needle guide 16 as shown in FIG. 3a. This variable orientation of the radius of curvature may be desirable by the practitioner to more effectively aim the distal tip 36 of the piercing element 20 in order to achieve a more desirable orientation for access from primary vessel 24 to secondary vessel 26. In one version of this embodiment, the needle guide 34 is fabricated of a superelastic material, such as Nitinol, to achieve this curvature effect. However, it should be noted that the needle guide 34 need not necessarily be made of a superelastic material for this embodiment to function. Since the shape of the needle guide comes from the secondary lumen 14, its shape is determined by moving the primary lumen 18 axially.

Referring again to FIG. 3a, once the main body 12 is inserted into primary vessel 24 and advanced to the desired site determined by the practitioner using ultrasound or fluoroscopic imaging, as previously described, it may be desired to adjust the radius of curvature of needle guide 34 to increase the angle of the axis of distal tip 36 by rotating knob 4 of handle 2. Since piercing distal tip 36 is configured to have echogenic and radiopaque properties to allow the practitioner to visualize the orientation of piercing tip 36 under real time imaging guidance, and the main body 12 of device 10 is incrementally rotatable about its axis, this will allow the practitioner to more effectively aim piercing tip 36 through direct visualization as secondary blood vessel 26 is "nudged" by the atraumatic tip of the needle guide 16 of the device 10 as the main body is incrementally rotated and the radius of curvature as desired, to allow more accurate penetration from primary blood vessel 24 to secondary blood vessel 26.

Figure 4A:
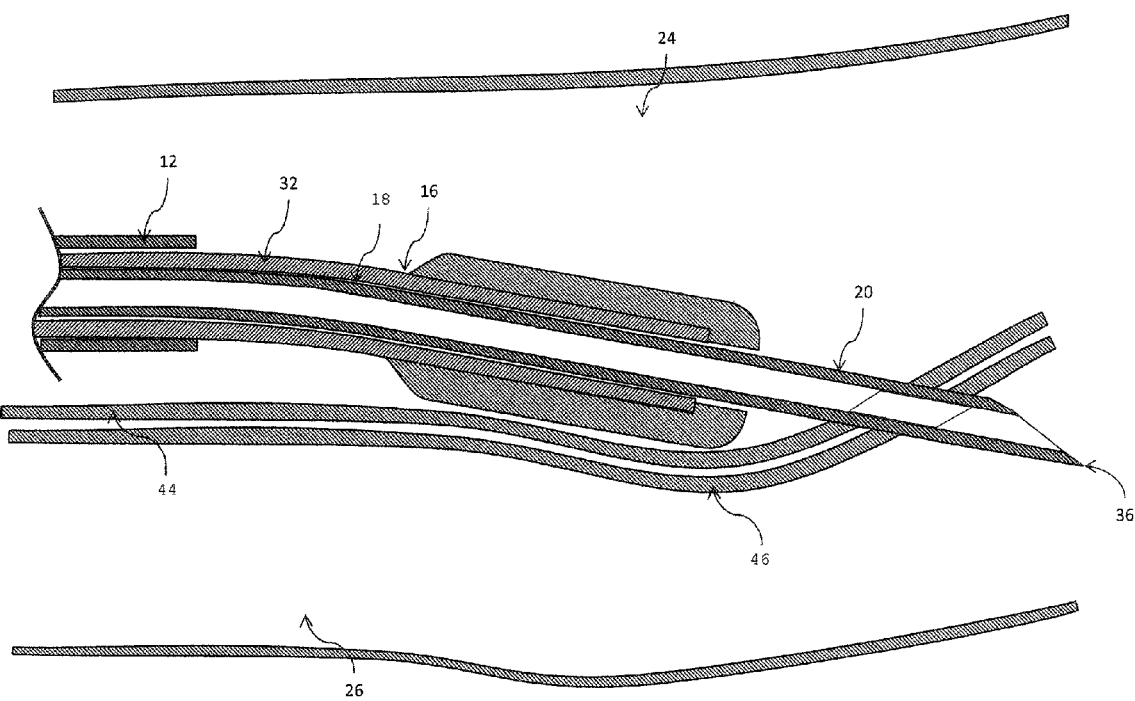
FIG. 4a is a view similar to FIG. 3a, wherein the piercing element is advanced from the primary blood vessel into the adjacent secondary blood vessel.
Figure 4B:
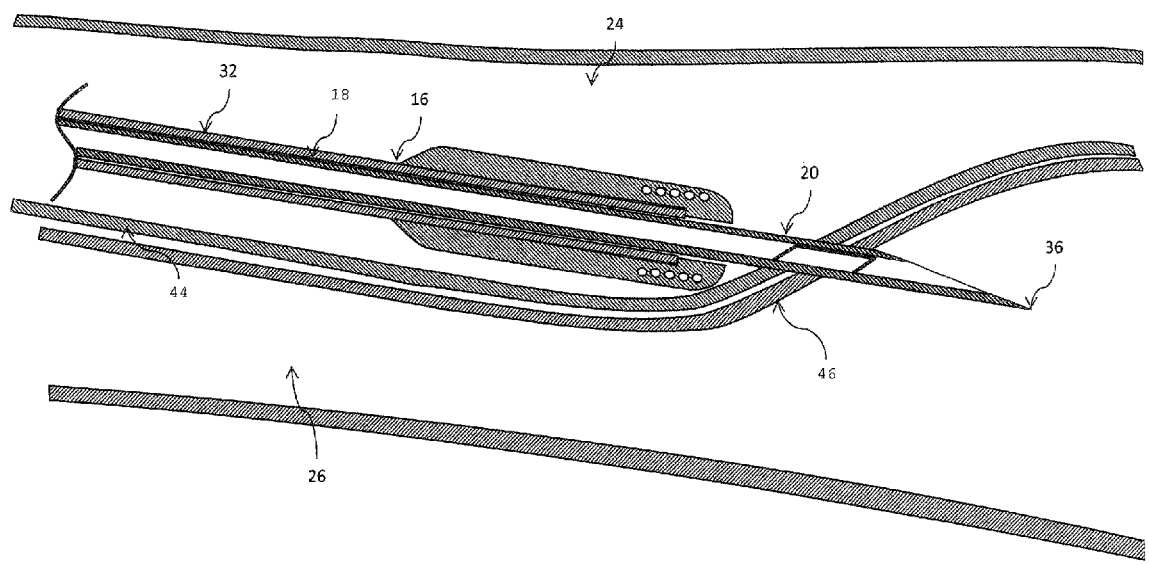
FIG. 4b is a view similar to FIG. 3b, wherein the piercing element is advanced from the primary blood vessel into the adjacent secondary blood vessel.

With reference now to FIG. 4a, once the practitioner has oriented piercing tip 36 as desired for optimal penetration, knob 4 of handle 2 is advanced to penetrate from primary blood vessel 24 through the primary vessel wall 44 to secondary blood vessel 26 through the secondary vessel wall 46. This may be done under direct imaging guidance to verify complete penetration without extending beyond the flow passage of blood vessel 26. The practitioner may also verify acceptable penetration through direct visualization of blood that flows through lumen 22 and exits aperture 4 of handle 2 as shown in FIG. 1.

Figure 5A:
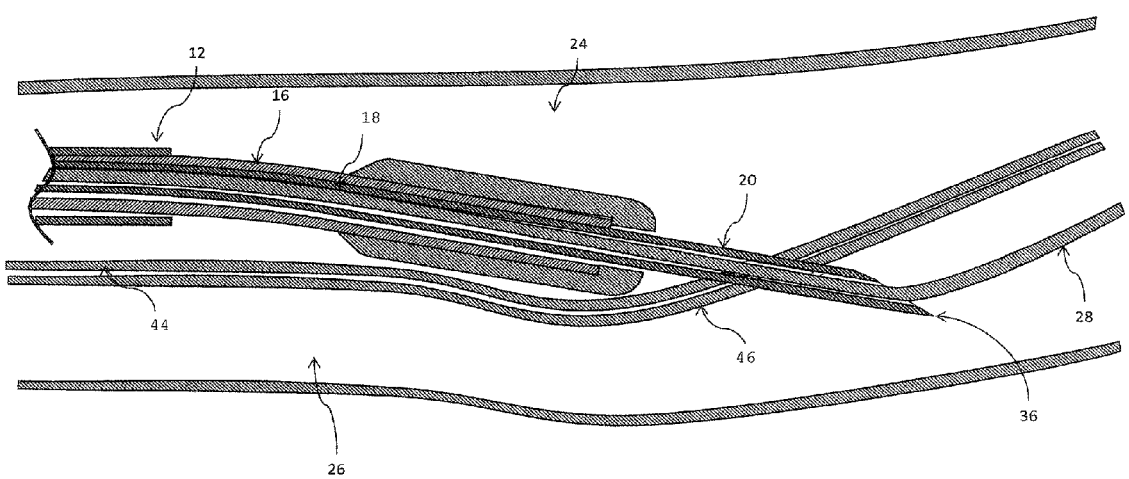
FIG. 5a is a view similar to FIG. 4a, wherein a guidewire is extended from the primary blood vessel and into the adjacent secondary blood vessel.
Figure 5B:
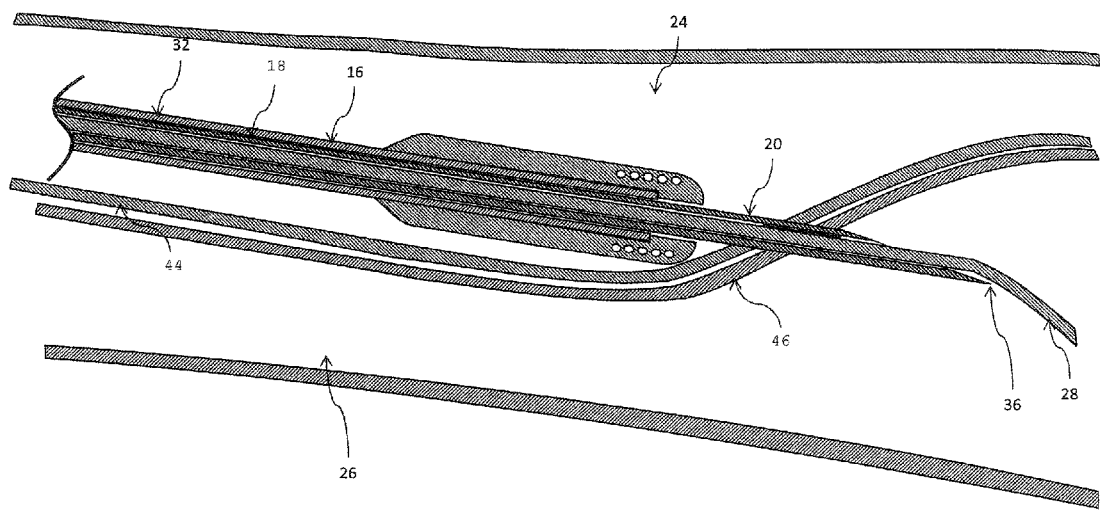
FIG. 5b is a view similar to FIG. 4b, wherein a guidewire is extended from the primary blood vessel and into the adjacent secondary blood vessel.
Figure 6:
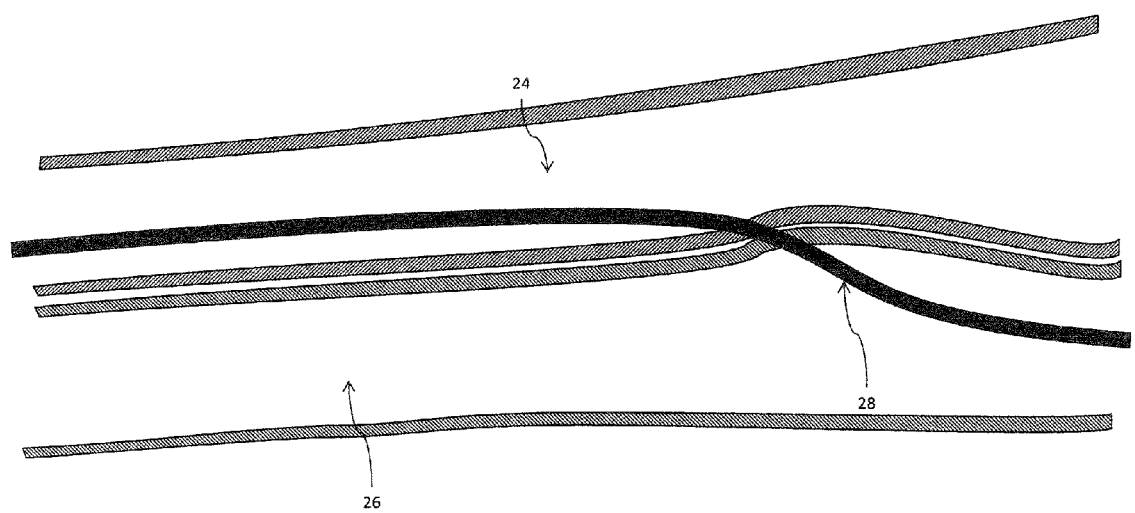
FIG. 6 illustrates the small communicating aperture and the guidewire placement created by the device and methods of the present invention after either embodiment of the inventive device of FIGS. 1a-5b has been withdrawn from the procedural site.

With reference now to FIG. 5a, once penetration from primary blood vessel 24 to secondary blood vessel 26 has been achieved, a guidewire 28, preferably having a diameter of 0.014" or less, is advanced through an aperture 6 of the handle 2 until the guidewire is positioned in the blood flow path of blood vessel 26 sufficiently to allow device 10 to be removed while retaining its position in blood vessel 26. With reference now to FIG. 6, once guidewire 28 is sufficiently in position as previously described, the practitioner withdraws the device 10 completely from the body, thus leaving the guidewire in the desired position and crossing from primary vessel 24 to secondary vessel 26.

Figure 7:
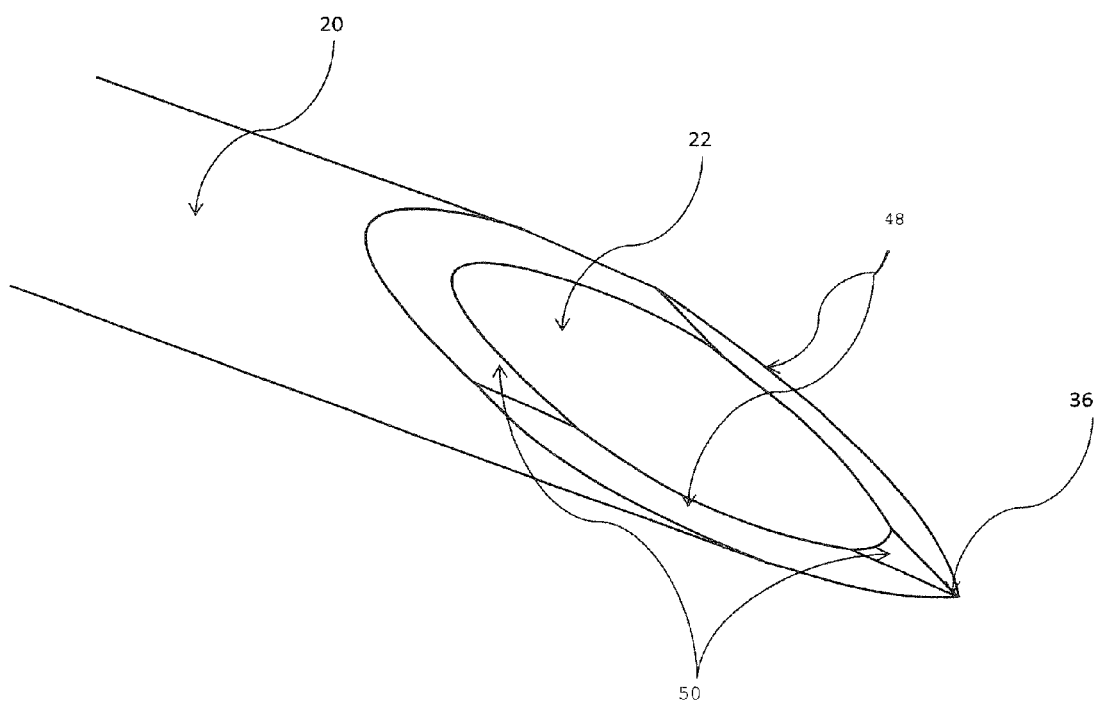
FIG. 7 illustrates an isolated detail view of the distal tip of the piercing element for the illustrated embodiments.

FIG. 7 illustrates a detail view of the configuration of the piercing tip 36 utilized in both of the illustrated embodiments. The tip is configured to have a lancet point 48 to enhance the penetration from primary blood vessel 24 to secondary blood vessel 26. A primary bevel 50 is ground at an angle between 12 and 20 degrees with a secondary angle between 5-20 degrees, with a rotation angle between 25-45 degrees. The needle grind is designed such that it pierces through the vessel wall and does not core, or cut a plug, through the vessel wall, to minimize bleeding between vessels when removed after the guidewire is placed into the secondary vessel. The outer diameter of the piercing member is also minimized to further reduce bleeding. The piercing member is oriented within the secondary lumen such that the tip of the lancet point is directed toward the adjacent secondary vessel. Other piercing mechanisms, or needle point grind configurations, known to those skilled in the art may be provided.

The embodiment of FIGS. 1*b*, 2*b*, 3*b*, 4*b*, and 5*b* (the "B" embodiment) is similar in most respects to that of FIGS. 1*a*, 2*a*, 3*a*, 4*a*, and 5*a* (the "A" embodiment), differing only in the details to be explained below. All common elements to those in the A embodiment are identified by common reference numerals in the figures illustrating the B embodiment, and the method sequencing shown in FIGS. 2*b*, 3*b*, 4*b*, and 5*b* is similar to that shown in FIGS. 2*a*, 3*a*, 4*a*, and 5*a*. FIGS. 6 and 7 are common to both embodiments.

Figure 3B:
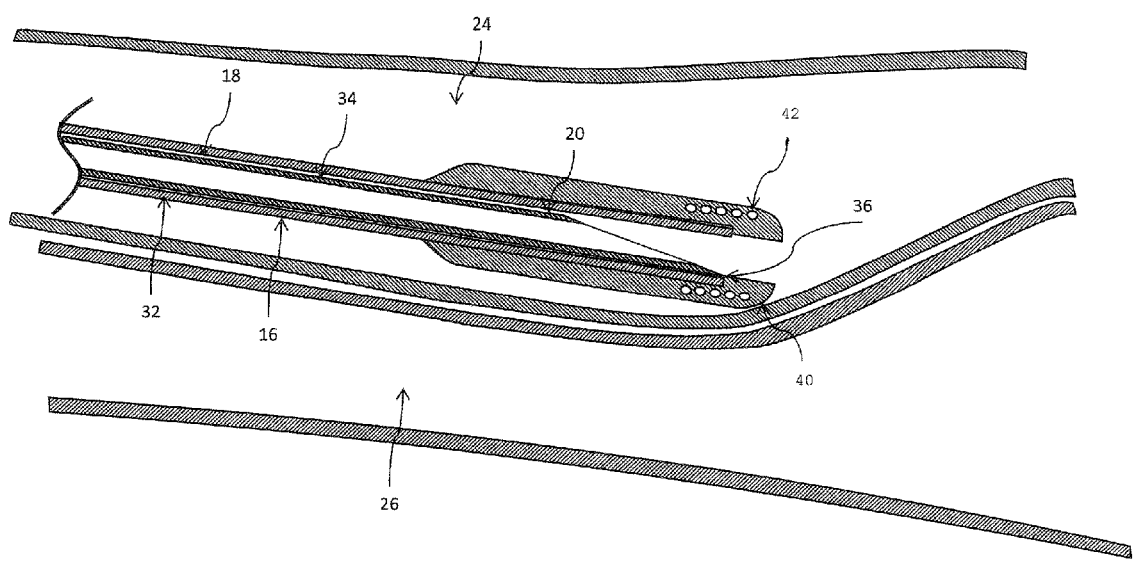
FIG. 3b is a view similar to FIG. 2b, wherein the distal piercing element of FIG. 2b has been advanced distally to push the blood vessel in which it is disposed into contact with the adjacent blood vessel.

The major difference between the A and B embodiments is that in the B embodiment the primary lumen 14 has been eliminated. This is because, in this embodiment, the shape of the needle guide 34 is not adjustable. Thus, it remains straight, and need not be fabricated of superelastic material. This arrangement is possible because the blunt tip 40 may be manipulated by the practitioner to ensure that the adjacent vessel walls of the primary and secondary vessel may be pierced by an axial advancement of the piercing member, as shown in FIG. 3*b*. As a result of this change, the knob 4 has also been eliminated, since control of the curvature of needle guide 34 is not required.

Accordingly, although an exemplary embodiment and method according to the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A device for creating intravascular access and guidewire placement, comprising:
   a main body having a first lumen;
   a piercing member disposed in said first lumen, and configured to be moved distally out of said first lumen and to pierce through tissue while being distally moved, said piercing member having a sharp point on one end thereof and being retractable into the first lumen;
   a handle attached to said main body and having an actuator for moving said piercing member;
   a second lumen within the piercing member;
   a third lumen within said main body, outwardly of the first lumen; and
   a guidewire disposed in said second lumen for delivery into a desired site from a distal end of said second lumen;
   wherein the first lumen is defined by a needle guide having shape memory properties, the needle guide being actuatable to a curved orientation by adjustment of a position of the main body to create an incrementally adjustable radius of curvature on the needle guide, the needle guide comprising an atraumatic distal tip having blunt walls with a thickness substantially greater than a thickness of walls defining the needle guide which are proximal to the atraumatic distal tip.

2. The device as recited in claim 1, wherein the piercing member has shape memory properties, and is actuatable to create an incrementally adjustable radius of curvature.

3. The device as recited in claim 1, and further comprising an actuator on said handle for actuating the needle guide to a curved orientation.

4. The device as recited in claim 3, wherein said actuator comprises a rotatable knob.

5. The device as recited in claim 1, wherein said actuator comprises a slide.

6. The device as recited in claim 1, wherein said atraumatic distal tip comprises radiopaque materials.

7. The device as recited in claim 6, wherein the radiopaque materials comprise a plurality of coils constructed of a radiopaque material.

8. A device for creating intravascular access and guidewire placement, comprising:
   a main body having a first lumen, said first lumen being defined by a needle guide having an atraumatic distal tip;
   a piercing member disposed in said lumen, and configured to be moved distally out of said lumen and to pierce through tissue while being distally moved;
   a handle attached to said main body and having an actuator for moving said piercing member;
   a second lumen within the piercing member; and
   a guidewire disposed in said second lumen for delivery into a desired site from a distal end of said second lumen;
   wherein said atraumatic distal tip comprises a plurality of coils constructed of a radiopaque material.

* * * * *